(12) United States Patent
Kovanyine Lax et al.

(10) Patent No.: US 8,507,513 B2
(45) Date of Patent: Aug. 13, 2013

(54) PROCESS FOR THE PREPARATION OF ROSUVASTATIN SALTS

(75) Inventors: Gyoergyi Kovanyine Lax, Budapest (HU); Eva Sipos, Budapest (HU); Jozsef Barkoczy, Budapest (HU); Balazs Volk, Budapest (HU); Gyula Simig, Budapest (HU); Ferenc Bartha, Tiszavasvari (HU); Gyoergy Ruzsics, Hoegyesz (HU); Adrienn Karasz, Budapest (HU); Imre Kiraly, Salgotarjan (HU); Kalman Nagy, Budapest (HU)

(73) Assignee: Egis Gyogyszergyar Nyilvanosan Muekoedoe Reszvenytarsasag, Budapest (HU)

( * ) Notice: Subject to any disclaimer, the term of this patent is extended or adjusted under 35 U.S.C. 154(b) by 0 days.

(21) Appl. No.: 13/143,943

(22) PCT Filed: Jan. 15, 2010

(86) PCT No.: PCT/HU2010/000007
§ 371 (c)(1),
(2), (4) Date: Nov. 2, 2011

(87) PCT Pub. No.: WO2010/082072
PCT Pub. Date: Jul. 22, 2010

(65) Prior Publication Data
US 2012/0116082 A1 May 10, 2012

(30) Foreign Application Priority Data

Jan. 15, 2009 (HU) .................................. 0900019
Jul. 24, 2009 (HU) .................................. 0900460

(51) Int. Cl.
*A01N 43/54* (2006.01)
*A61K 31/505* (2006.01)
(52) U.S. Cl.
USPC .......................................... 514/275; 544/332
(58) Field of Classification Search
USPC ........................................... 514/275; 544/332
See application file for complete search history.

(56) References Cited

U.S. PATENT DOCUMENTS

| | | | |
|---|---|---|---|
| 7,129,352 B2 * | 10/2006 | Taylor et al. ................. | 544/297 |
| 7,396,927 B2 * | 7/2008 | Niddam-Hildesheim et al. ............................. | 544/297 |
| 7,842,807 B2 * | 11/2010 | Horbury et al. ............... | 544/297 |
| 2005/0131066 A1 * | 6/2005 | Niddam-Hildesheim et al. ............................. | 514/548 |
| 2007/0105882 A1 * | 5/2007 | Black et al. ................... | 514/275 |
| 2008/0249120 A1 * | 10/2008 | Soni et al. ..................... | 514/275 |
| 2009/0111839 A1 * | 4/2009 | Zlicar et al. ................... | 514/275 |
| 2009/0275752 A1 * | 11/2009 | Reddy et al. .................. | 544/297 |
| 2010/0056783 A1 * | 3/2010 | Satyanarayana Reddy et al. ............................. | 544/297 |
| 2012/0059022 A1 * | 3/2012 | Booth et al. .................. | 514/275 |

FOREIGN PATENT DOCUMENTS

| | | | |
|---|---|---|---|
| IN | 2006MU01654 | * | 7/2008 |
| IN | 2007MU00300 | * | 10/2008 |
| WO | WO 2008015563 A2 | * | 2/2008 |
| WO | WO 2010081861 A1 | * | 7/2010 |

* cited by examiner

*Primary Examiner* — James O Wilson
*Assistant Examiner* — Alexander R Pagano
(74) *Attorney, Agent, or Firm* — Jonathan Myers; Andrew Wilford

(57) ABSTRACT

The present invention relates to a new process for the preparation of rosuvastatin [7-[4-(4-Fluorophenyl)-6-isopropyl-2-(methanesulphonyl-methyl-amino)-pyrimidin-5-yl]-(3R,51S)-dihydroxy-hept-6-enoic acid] of the formula (I) salts formed with bivalent cations, preferably with calcium or zinc ions, characterized in that rosuvastatin tert.-butylammonium salt is reacted with the appropriate bivalent cation, preferably with calcium or zinc ions in a mixture of a water immiscible or slightly miscible organic solvent and water and the formed salt is isolated.

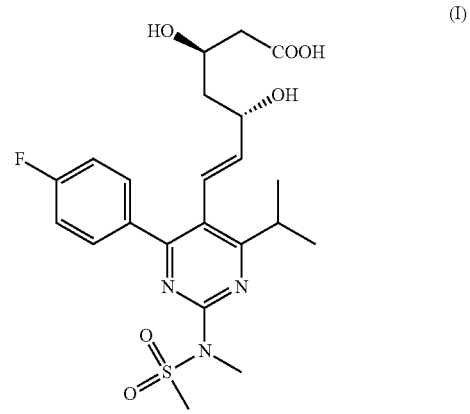

(I)

16 Claims, No Drawings

PROCESS FOR THE PREPARATION OF ROSUVASTATIN SALTS

CROSS REFERENCE TO RELATED APPLICATIONS

This application is the US-national stage of PCT application PCT/HU2010/000007 filed 15 Jan. 2010, published 22 Jul. 2010 as WO2010/082072, and claiming the priority of Hungarian patent application P 09 00019 itself filed 15 Jan. 2009 and Hungarian patent application P 09 00460 itself filed 24 Jul. 2009, whose entire disclosures are herewith incorporated by reference.

FIELD OF THE INVENTION

The present invention relates to methods for the preparation of pharmaceutically acceptable salts of (+)-7-[4-(4-fluorophenyl)-6-isopropyl-2-(methanesulfonyl-methyl-amino)-pyrimidin-5-yl]-(3R,5S)-dihydroxy-hept-6-enoic acid of the formula

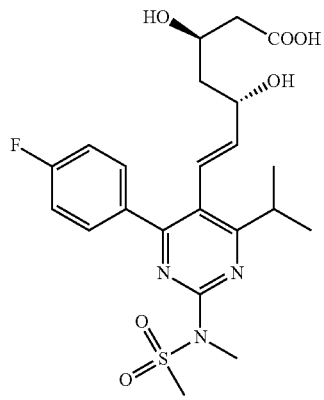

(+)-7-[4-(4-fluorophenyl)-6-isopropyl-2-(methanesulfonyl-methyl-amino)-pyrimidin-5-yl]-(3R,5S)-dihydroxy-hept-6-enoic acid of the formula (I) having the International Nonproprietary Name (INN) rosuvastatin, which is a pharmaceutically active ingredient for the regulation of lipid metabolism. The effect of rosuvastatin is the inhibition of the enzyme 2-hydroxy-2-methyl-glutaryl-coenzyme-A reductase in the liver, thus reducing the rate of the biosynthesis of the cholesterol and the cholesterol level in the blood-plasma. Rosuvastatin of the formula (I) is used mostly in its salt forms for the treatment of hypercholesteremia, hyperlipoproteinemia and atheriosclerosis.

The object of the present invention is method the preparation of (+)-7-[4-(4-fluorophenyl)-6-isopropyl-2-(methanesulfonyl-methyl-amino)-pyrimidin-5-yl]-(3R,5S)-dihydroxy-hept-6-enoic acid calcium salt (2:1) of the formula (II)

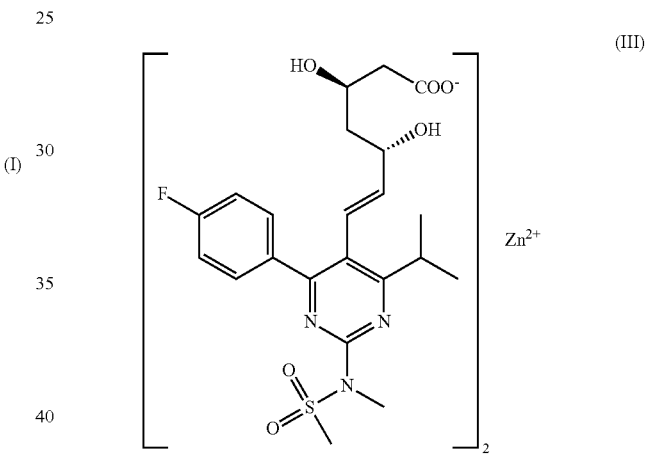

and (+)-7-[4-(4-fluorophenyl)-6-isopropyl-2-(methanesulfonyl-methylamino)-pyrimidin-5-yl]-(3R,5S)-dihydroxy-hept-6-enoic acid zinc salt (2:1) of the formula (III)

from (+)-7-[4-(4-fluorophenyl)-6-isopropyl-2-(methane-sulfonyl-methyl-amino)-pyrimidin-5-yl]-(3R,5S)-dihydroxy-hept-6-enoic acid tert.-butylammonium salt of the formula (IV)

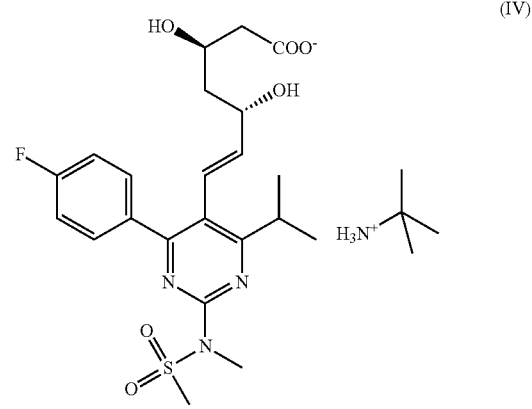

in which the product is directly formed from the compound of the formula (IV) and the compound of the formula (II) or (III) is obtained from a medium comprising organic solvent.

TECHNICAL BACKGROUND OF THE INVENTION

The compound of (+)-7-[4-(4-fluorophenyl)-6-isopropyl-2-(methane-sulfonyl-methyl-amino)-pyrimidin-5-yl]-(3R,5S)-dihydroxy-hept-6-enoic acid (rosuvastatin) is known from the prior art. It was described for the first time in European Patent No. 521471 in acid form and in the forms of some pharmaceutically acceptable salts including calcium salt of the formula (II) and ammonium salt. The zinc salt of rosuvastatin (2:1) of the formula (III) was described first in the Hungarian patent application P0600293 and in international patent application No. WO2007/119085.

According to the process described in the European patent No. 521471 rosuvastatin salts are prepared by saponification of rosuvastatin alkyl esters of the general formula (V),

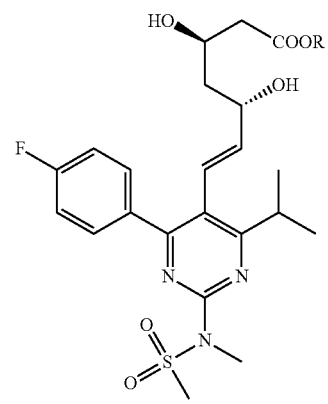

(V)

the thus obtained rosuvastatin salt is optionally converted to free acid and the obtained salt or acid is converted to a pharmaceutically acceptable salt, preferably to calcium salt.

Several processes are known from the prior art wherein rosuvastatin calcium salt of the formula (II) is prepared via different intermediates. The process via a rosuvastatin ketal intermediate compound of the general formula (VI)

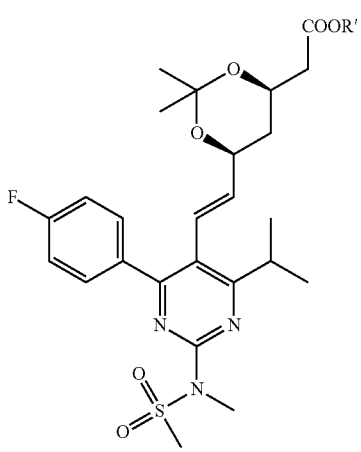

(VI)

is described in International Patent Applications WO 2006/126035 and WO 2005/042522, while the ketal acid salts according to the formula (VII)

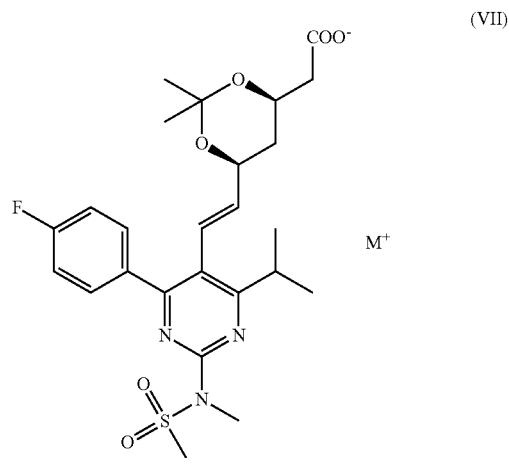

(VII)

M = Na, K, stb.

and the rosuvastatin ketal acid of the formula (VIII)

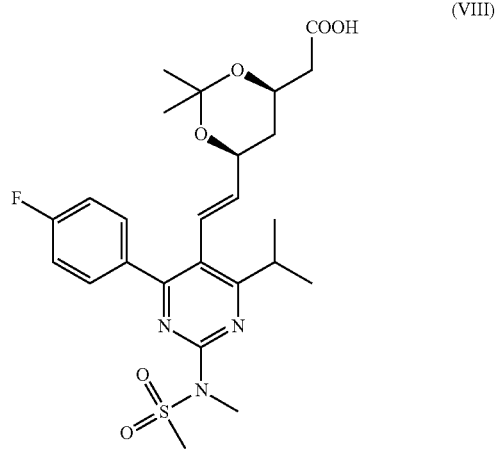 [SMILES: CC(C)c1nc(N(C)S(C)(=O)=O)nc(-c2ccc(F)cc2)c1/C=C/[C@@H]1C[C@H](CC(=O)O)OC(C)(C)O1]

(VIII)

are disclosed as intermediates in International Patent Application WO 2006/126035. Processes using the compound of the formula (V) as starting compound are described e.g. in International Patent Applications WO 2003/097614 and WO 2005/023778. A process for the preparation of calcium salt from rosuvastatin lactone of the formula (IX)

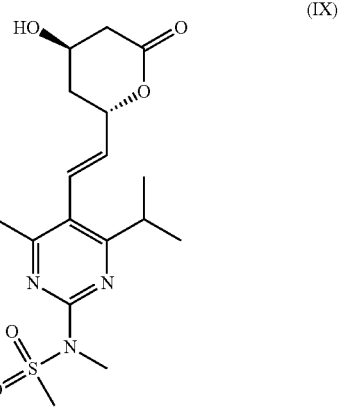

(IX)

is described in International Patent Applications WO 2005/040134, WO 2005/077916 and WO 2006/136407.

According to the prior art there are processes in which rosuvastatin calcium salt of the formula (II) is prepared from any of the rosuvastatin salts formed with amines. A common feature of these processes known from the prior art is that rosuvastatin calcium salt of the formula (II) is separated from aqueous media.

As known from prior art, the conversion is carried out by the following method: a salt of rosuvastatin formed with an amine is converted to a sodium salt, then in an aqueous solution a calcium salt is obtained from the sodium salt and the calcium salt is isolated.

In most of the cases described in prior art, preparation starting from salts formed with amines is carried out via the sodium salt of rosuvastatin. International Patent Application WO 01/060804 describes crystalline forms of ammonium, methyl-ammonium, ethyl-ammonium, diethanol-ammonium, tris-(hydroxymethyl)-methyl ammonium, benzylammonium and 4-methoxybenzylammonium salts of rosuvastatin. Furthermore, the conversion of these crystalline salts into rosuvastatin calcium salt is also disclosed in such a manner that the ammonium salts are converted to rosuvastatin sodium salt with sodium hydroxide in an aqueous medium, then the product is converted to calcium salt of the formula (II) and the product is filtered off from the aqueous solution. The purity of the product is not mentioned in the description.

International Patent Application No. WO 2005/051921 discloses the purification of rosuvastatin calcium salt via crystalline forms of isopropyl- or cyclohexyl-ammonium salts in several steps. Rosuvastatin calcium salt is converted to rosuvastatin of the formula (I), then it is transformed into its isopropyl- or cyclohexyl-ammonium salt using ethyl acetate as solvent. The rosuvastatin calcium salt is obtained through rosuvastatin sodium salt from rosuvastatin ammonium salts mentioned above after filtration from an aqueous solution with a 73.6% yield. However, the purity of the product has not been disclosed.

International Patent Application No. WO 2005/077916 discloses crystalline forms and amorphous forms of rosuvastatin cyclohexyl-, dicyclohexyl-, isopropyl-, diisopropyl- and (S)-1-methylbenzyl-ammonium salts. The listed salts are transformed into rosuvastatin calcium salt of the formula (II) in such a manner that rosuvastatin ammonium salt is converted to rosuvastatin lactone of the formula (IX), which is converted to sodium salt and reacted with a calcium source in an aqueous medium, then the amorphous rosuvastatin calcium salt is filtered off. Furthermore, the description discloses a recrystallisation process for the purification of rosuvastatin ammonium salts and the rosuvastatin calcium salt obtained from them with a purity higher than 99.5%. The amount of the diastereomer impurity is high, according to said patent application the amount of the impurity can be reduced to about 0.25% if the process disclosed is used. However, the active ingredient having the above-mentioned purity does not meet the limits of the internationally accepted ICH requirements because the highest acceptable amount of the impurity is 0.15%.

International Patent Application No. WO 2008/067440 discloses the dehydroabietine salt of rosuvastatin from which rosuvastatin calcium salt is prepared through sodium salt in water. The product is filtered off from an aqueous solution. The HPLC purity of the rosuvastatin calcium salt according to the example is 99.80%, the amount of diastereomer impurity is 0.14%, which is near to the accepted limit of 0.15%.

The above-mentioned patent applications do not disclose the tert-butylammonium salt of rosuvastatin of the formula (IV). International Patent Applications WO 2007/125547 and WO 2008/044243 disclose a new process for the preparation of rosuvastatin tert-butylammonium salt and for the preparation of rosuvastatin calcium salt in an aqueous solution via rosuvastatin sodium salt and isolating by filtration. The purity of the product is not mentioned.

The conversion of different rosuvastatin ammonium salts to calcium salt directly instead of converting via sodium salt is disclosed in International Patent Applications WO 2004/014872 and WO 2006/136407. The reaction is carried out in water according to the inventors of both inventions.

International Patent Application WO 2004/014872 protects a process using special process parameters which result in an increased efficiency of the filtration of the precipitated salt. In course of the process, the rosuvastatin calcium salt is obtained from certain water soluble salts of ammonium compounds with rosuvastatin (ammonium, tris-(hydroxymethyl)-methylammonium, methylammonium) by addition of calcium chloride to them and the filtration off from the aqueous solution. The purity of the product is not mentioned in the description.

International Patent Application WO 2006/136407 discloses a process for the preparation of rosuvastatin calcium salt free from contaminants. In course of the process, a rosuvastatin ester is hydrolyzed in a mixture of water and an aprotic solvent and the obtained ammonium salt (e.g. isopropylammonium, N-methylcyclohexylammonium etc.) is boiled in water with a calcium source and rosuvastatin calcium salt is obtained free from alkali metals, in the purity of 99.9% (HPLC). The HPLC purity given by the authors refers to the product before drying. The tert.-butylammonium salt of rosuvastatin is not mentioned among the used starting compounds according to the application.

Rosuvastatin zinc salt is the subject of our Hungarian patent application No. P0600293 and our International Patent Application WO 2007/119085. In our Hungarian patent application No. P0700667 processes were disclosed for the preparation of rosuvastatin zinc salt of the formula (III), wherein rosuvastatin of the formula (I) or a sodium salt thereof, alkylester of rosuvastatin of the formula (V), rosuvastatin lactone of the formula (IX) or rosuvastatin ketal ester of the formula (VI) were used as starting compound.

International Patent Application WO2008/015563 discloses a process for the preparation of rosuvastatin zinc salt of the formula (III) from tert-butylammonium salt of rosuvastatin via sodium salt by filtration of the product from an aqueous solution. The purity of the zinc salt is 99.41%.

There is no other process mentioned in the prior art for the preparation of rosuvastatin zinc salt of the formula (III) from rosuvastatin ammonium salts.

SUMMARY OF THE INVENTION

Strict quality requirements apply to the pharmaceutical active ingredients of pharmaceutical compositions, some of them relating to the chemical purity and stability of the active ingredient. In connection with pharmaceutical compositions, further requirements of the authorities are the production of the composition in an acceptable quality and proven stability thereof. These requirements are disclosed and published in the appropriate paragraphs of pharmacopoeias. The compliance with the quality requirements for the pharmaceutical compositions and pharmaceutical active ingredient is a basic requirement of the marketing authorisation of a pharmaceutical composition. In connection with the use of rosuvastatin as a pharmaceutical composition, basic requirements are the high purity, appropriate stability and ease of formulation.

During our research and development work for the preparation of calcium salt of rosuvastatin, we found that it was not possible to prepare a product having a purity and moisture content acceptable for the preparation of a pharmaceutical composition according to processes known from prior art.

We found that in course of the processes carried out in an aqueous medium according to prior art a considerable amount, 0.25-0.30% (HPLC) of rosuvastatin lactone of the formula (IX) is formed. The yields of these process variations are about 60-80% only and the product prepared from tert-butylammonium salt of rosuvastatin contained a considerable amount (2000-3000 ppm) of tert-butylamine and alkali ion contaminants. Furthermore, even if the product filtered from aqueous media has an acceptable purity examined by HPLC, the drying of the product was found to be problematic. The product contains approximately 10% of water even if it is dried at 50° C. in high vacuum for 6 hours. In case of using a longer drying period or higher temperature, the amount of the lactone contaminant increases by more than 0.50%, meanwhile the specification of the originator company allows only 0.22% of this contaminant even in the pharmaceutical composition. For example, the amount of the lactone contaminant of rosuvastatin calcium salt filtered off from water and dried at 80° C. for 2 hours is 0.22%, after 10 hours 0.67%.

We found that even after a long-term drying the product contained so much water that makes it difficult to use it in course of the processes for the preparation of pharmaceutical compositions. Under conditions of strong drying, which is necessary for the preparation of essential dry product, the amount of the lactone of the formula (IX) and the 5-oxo contaminant according to the formula (X)

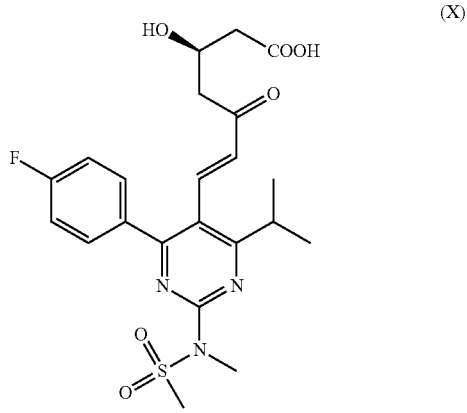 [SMILES: CC(C)c1nc(N(C)S(C)(=O)=O)nc(-c2ccc(F)cc2)c1/C=C/C(=O)C[C@@H](O)CC(=O)O]

having the chemical name (+)-7-[4-(4-fluorophenyl)-6-isopropyl-2-(methanesulphonyl-methyl-amino)-pyrimidin-5-yl]-(3R)-hydroxy-5-oxo-hept-6-enoic acid (respectively its calcium or zinc salt) increases. In light of the aforesaid it is a very important fact that documents of the prior art do not mention the purity and water content after drying the rosuvastatin calcium salts prepared from an aqueous solution.

The direct conversion of different rosuvastatin ammonium salts to rosuvastatin calcium salt is described in International Patent Applications WO 2004/014872 and WO 2006/136407 which are discussed above in detail. The reaction is carried out in water by the inventors of both inventions. Authors of International Patent Application WO 2004/014872 do not mention the purity of the product, while the authors of International Patent Application WO 2006/136407 disclose the purity of the product only before drying. There are no any data in the prior art documents about the amounts of the corresponding amine or ammonium ion contaminants in the rosuvastatin calcium salt prepared from rosuvastatin ammonium salts. During our research and development work, we examined several process variants which used tert-butylammonium salt of rosuvastatin as starting material and which are based on the reaction of tert-butylammonium salt of rosuvastatin with calcium ions in aqueous solution. The processes and analytical data of the products prepared according to the prior art are shown in reference Examples 6 and 7. The purities of these products corresponded to the data indicated in the patent applications but the tert.-butylamine content was unacceptably high (40000 and 62000 ppm, respectively).

The above-mentioned reactions were carried out in ethanol either with the use of calcium chloride or with the use of calcium acetate, but in both cases, the yields were very low.

Our aim was to develop a chemical process for the preparation of rosuvastatin calcium salt of the formula (H) and rosuvastatin zinc salt of the formula (III) using rosuvastatin tert.-butylammonium salt of the formula (IV) as starting compound, which process can be reproduced on industrial scale with a good yield and a high purity, the product obtained is free from alkali metals and tert-butylamine, free from water in an adequate manner (water content is below 3 weight %) and is suitable for formulation.

In relation to the purity of the active ingredient, our objective was to minimalize the amount of rosuvastatin lactone of the formula (IX) and the 5-oxo compound of (+)-7-[4-(4-fluorophenyl)-6-isopropyl-2-(methanesulphonyl-methyl-amino)-pyrimidin-5-yl]-(3R)-hydroxy-5-oxo-hept-6-enoic acid (or the calcium or zinc salt thereof, respectively) during the process and the drying.

The above-mentioned aim is solved according to present invention.

DETAILED DESCRIPTION OF THE INVENTION

The present invention relates to a process for the preparation of (+)-7-[4-(4-fluorophenyl)-6-isopropyl-2-(methansulfonyl-methyl-amino)-pyrimidin-5-yl]-(3R,5S)-dihydroxy-hept-6-enoic acid calcium salt (2:1) of the formula (II) and (+)-7-[4-(4-fluorophenyl)-6-isopropyl-2-(methansulfonyl-methyl-amino)-pyrimidin-5-yl]-(3R,5S)-dihydroxy-hept-6-enoic acid zinc salt (2:1) of the formula (III) in high purity which is reproducible on industrial scale.

In course of the process 7-[4-(4-fluorophenyl)-6-isopropyl-2-(methanesulphonyl-methyl-amino)-pyrimidin-il]-(3R,5S)-dihydroxy-hept-6-en acid tert.-butyl-ammonium salt of the formula (IV) is used as starting compound.

We found surprisingly that if the end product is obtained from an organic solvent instead of an aqueous medium, essential improvements are achieved as follows:
- the amount of the lactone contaminant of the product is considerably lower;
- the difficulties of the drying of the wet active ingredient can be eliminated, the water content of the rosuvastatin calcium salt can be reduced from the usual 4-5% even below 1%;
- the yield of the process in special cases rises from 60-80% over 95%;
- the tert.-butylamin content of the product can be reduced considerably, instead of the amount of 2000-7000 ppm of the product filtered from aqueous media even under 100 ppm;
- lactone content of the product is under 0.15% even after drying.

The preparation of the high-purity rosuvastatin calcium salt of the formula (II) with low, even lower than 1.5% of water content and high-purity rosuvastatin zinc salt of the formula (III) having a low, even lower than 2% of water content was not possible using any of the processes disclosed by prior art.

The water content of the rosuvastatin salts is crucial. We found that the rosuvastatin calcium salt of the formula (II) having low water content and the rosuvastatin zinc salt of the formula (III) having low water content according to the present invention showed considerably lower decomposition rates during the drying and the stability tests than the salts obtained from aqueous media according to the prior art. This effect can be explained with the fact that the water content of the active ingredient has an important role during the decomposition. The most important decomposition products are the rosuvastatin lactone of the formula (IX) and the 5-oxo compound of the formula (X), namely (+)-7-[4-(4-fluorophenyl)-6-isopropyl-2-(methanesulphonyl-methyl-amino)-pyrimidin-5-yl]-(3R)-hydroxy-5-oxo-hept-6-enoic acid.

During the stability test of the rosuvastatin salts of the formula (II) prepared according to the prior art the most significant decomposition product was the 5-oxo compound of the formula (X). In case of the rosuvastatin calcium salt of the formula (II) obtained by filtration from water, the amount of the 5-oxo contaminant increased from the initial amount of 0.10% to 0.33% during storage at 40° C./75% humidity for three months which indicates considerable decomposition. Using an inert atmosphere, the decomposition could be reduced to 0.24%. However, decomposition occurs not only during the stability tests. We found that after the preparation of the product, the drying done with the purpose to eliminate water caused considerable lactonisation: The product contained 0.67% of lactone contaminant already after drying at 80° C., under $10^{-2}$ Hgmm pressure for ten hours (Table 1)

Rosuvastatin calcium salt of the formula (II) prepared according to the present invention in a two-phase medium containing water and ethyl acetate decomposed considerably less either in the course of drying or during the stability test. Using similar conditions for the drying the lactone content was 0.16% only.

In case of the rosuvastatin zinc salt of the formula (III) the most significant decomposition product is rosuvastatin lactone of the formula (IX). In case of rosuvastatin zinc salt according to the formula (III) obtained by filtration from water the initial amount of the lactone contaminant is high, 0.24% and it is increased to 0.63% during storage at 40° C., 75% humidity for three months, which indicates the considerable decomposition. However, decomposition occurs not only during the stability tests. We found that after the preparation of the product, during the drying carried out for the elimination of water caused considerably lactonisation. The product obtained by filtration from water contained 0.51% of lactone contaminant after a drying at 25° C. and under 1 Hgmm pressure for 2 hours, then for further 5 hours at 50° C. and under 1 Hgmm pressure. Meanwhile, rosuvastatin zinc salt of the formula (III) prepared according to the present invention in a two-phase medium containing water and ethyl acetate decomposed considerably less either in course of drying or during stability test. The product prepared according to the present invention contained less lactone contaminant (0.04%) before drying and in course of drying under similar conditions this value increased to 0.13% only. (Table 2)

TABLE 1

Drying data of rosuvastatin calcium salt

|  |  | Initial | 80° C./$10^{-2}$ Hgmm after 10 hours |
|---|---|---|---|
| Rosuvastatin calcium salt obtained from water (according to reference example 3)# | Lactone Water content | 0.05% 50.51% | 0.67% 0.01% |
| Rosuvastatin calcium salt according to the example 9 of the present invention# | Lactone Water content | 0.03% 2.45% | 0.16% 0.23% |

The drying of the product was carried out under the conditions indicated in this table.

TABLE 2

Drying data of rosuvastatin zinc salt

|  |  | Initial | 25° C./1 Hgmm for 2 hours then 50° C./1 Hgmm for 5 hours |
|---|---|---|---|
| Rosuvastatin zinc salt obtained from water (according to reference example 5)# | Lactone Water content | 0.12% >20.1% | 0.51% 2.20 |
| Rosuvastatin zinc salt according to the example 11 of the present invention# | Lactone Water content | 0.04% 1.90% | 0.13% 0.87% |

The drying of the product was carried out under the conditions indicated in this table.

According to the present invention the preparation of rosuvastatin calcium salt of the formula (II) is carried out in such a way that a biphase mixture of a water immiscible solvent and water is added to the rosuvastatin tert-butylammonium salt, preferably a two-phase mixture of ethyl acetate and water in a ratio of 5:1-5:4 (v/v), more preferably a mixture of ethyl acetate and water in a rate of 3:2 (v/v) is used at a temperature between 0° C. and 50° C. Based on the molar quantity of the starting compound, 0.45-50 molar equivalent of calcium ion source is added in 1-10 portions in solid state or in the form of an aqueous solution thereof. The mixture is kept under stirring for 0.01-10 hours, preferably for 0.1-2 hours at a temperature between 0 and 50° C., preferably between 20-40° C. Then the organic phase is separated, extracted with an aqueous solution of a water soluble calcium salt or calcium acetate and/or optionally with water, optionally the organic layer is dried with a desiccant and evaporated. The water content of the thus obtained rosuvastatin calcium is further decreased by addition and evaporation of ethyl acetate once or several times, then, the organic solvent is evaporated. The residual rosuvastatin calcium salt is stirred with an apolar solvent or a mixture thereof, preferably with hexane, heptane, petroleum ether, cyclohexane, toluene, tert-butyl-methyl ether, diisopropyl ether or diethylether or a mixture thereof, filtered and optionally washed with an apolar solvent.

According to the present invention, the preparation of rosuvastatin zinc salt of the formula (III) is carried out in such a way that a two-phase mixture of a water immiscible solvent and water is added at a temperature between 0° C. and 50° C. to the rosuvastatin tert-butylammonium salt. Preferably, a mixture of ethyl acetate and water in a proportion of 5:1-1:1 (v/v) is used. Based on the molar quantity of the starting compound, 0.45-20 molar equivalent of zinc ion source is added in 1-5 portions in solid state or as an aqueous solution thereof. The mixture is kept under stirring for 0.01-10 hours, preferably for 0.1-2 hours at a temperature between 0 and 50° C., preferably between 20-40° C. Then the organic phase is separated, extracted once or several times with an aqueous solution of a water miscible zinc salt and/or optionally with water, the organic layer is optionally dried with a desiccant, then evaporated. The water content of the obtained rosuvastatin salt is further decreased by addition and evaporation of ethyl acetate once or several times, then the organic solvent is evaporated. The residual rosuvastatin zinc salt is stirred with an apolar solvent or a mixture thereof, preferably with hexane, heptane, petroleum ether, cyclohexane, toluene, tert.-butyl-methyl ether, diisopropyl ether or diethyl ether or a mixture thereof, filtered and optionally washed with an apolar solvent.

Zinc and calcium salts used in the above-mentioned process variants for the preparation of rosuvastatin calcium salt of the formula (II) and rosuvastatin zinc salt of the formula (III) can be the calcium or zinc salts of inorganic or organic acids, or hydrate forms thereof, and calcium hydroxide, respectively.

For the preparation of rosuvastatin calcium salt of the formula (II), calcium hydroxide or an organic or inorganic calcium salt, e.g. a salt of calcium with formic acid, acetic acid, propionic acid, maleic acid, fumaric acid, succinic acid, lactic acid, malic acid, tartaric acid, citric acid, ascorbic acid, malonic acid, oxalic acid, glycolic acid, methanesulfonic acid, ethanesulphonic acid, a salt of calcium formed with an amino acid, calcium chloride or calcium nitrate can be used. Preferably calcium chloride or calcium acetate can be used.

For the preparation of rosuvastatin zinc salt of the formula (III), an organic or inorganic salt, e.g. a salt of zinc formed with formic acid, acetic acid, propionic acid, maleic acid, fumaric acid, succinic acid, lactic acid, malic acid, tartaric acid, citric acid, ascorbic acid, malonic acid, oxalic acid, glycolic acid, methanesulfonic acid, ethanesulphonic acid, a salt of zinc formed with an amino acid, zinc sulphate, zinc chloride, zinc bromide, zinc carbonate or zinc nitrate can be used. Preferably zinc sulphate, zinc chloride or zinc acetate can be used.

Further details of the present invention are shown in examples below without limiting the scope of the protection to the mentioned examples.

Example 1

7-[4-(4-Fluorophenyl)-6-isopropyl-2-(methane-sulphonyl-methyl-amino)-pyrimidin-5-yl]-(3R,5S)-dihydroxy-hept-6-enoic acid Calcium Salt (2:1)

Into a two-layer mixture of 10 ml of water and 15 ml of ethyl acetate 1.67 g (3.0 mmoles) of 7-[4-(4-fluorophenyl)-6-isopropyl-2-(methanesulphonyl-methyl-amino)-pyrimidin-5-yl]-(3R,5S)-dihydroxy-hept-6-enoic acid tert.-butylammonium salt is added under vigorous stirring at room temperature. After the complete dissolution of the starting compound 5×1.5 ml (5×7.5 mmoles) of a saturated calcium chloride solution are added dropwise at 15-minute intervals. After the dosage, the mixture is stirred for a further hour, then the upper layer containing ethyl acetate is separated and washed with 5 ml of 2M calcium chloride solution, then 2×5 ml of water. The dehydration of the organic layer is carried out by azeotropic distillation in such a way that the phase containing ethylacetate is evaporated to dryness and the obtained white residue is dissolved in anhydrous ethyl acetate. The solution is stirred for 5 minutes then evaporated to dryness at 42-45° C. under 50 mbar pressure. To the residue, 6 ml of cyclohexane is added and the suspension is stirred for 30 minutes. The solid product is filtered off, washed with 5 ml of anhydrous cyclohexane and dried at 50° C. for 7 hours under reduced pressure. Thus 1.30 g (87%) product is obtained.

HPLC purity: 99.90%.
Diastereomer contaminant: 0.01%.
Rosuvastatin lactone contaminant: 0.03%.
Tert.-butylamin content: <10 ppm.
Humidity: 0.95%.
IR (KBr): 3425, 1548, 1382, 1156, 965 cm$^{-1}$.
$^1$H-NMR (DMSO-d$_6$, 500 MHz): δ 7.71 (dd, J=8.7; 5.5 Hz, 2H), 7.26 (t, J=8.9 Hz, 2H), 6.52 (d, J=16.1 Hz, 1H), 5.71 (br s, 1H), 5.54 (dd, J=16.1; 5.4 Hz, 1H), 5.05 (b, 1H), 4.24 (m, 1H), 3.81 (m, 1H), 3.54 (s, 3H), 3.46 (s, 3H), 3.42 (m, 1H), 2.17 (m, 1H), 2.04 (m, 1H), 1.51 (m, 1H), 1.33 (m, 1H), 1.21 (d, J=6.6 Hz, 6H) ppm.

Example 2

7-[4-(4-Fluorophenyl)-6-isopropyl-2-(methane-sulphonyl-methyl-amino)-pyrimidin-5-yl]-(3R,5S)-dihydroxy-hept-6-enoic acid Calcium Salt (2:1)

Into a two-layer mixture of 10 ml of water and 15 ml of ethyl acetate 1.67 g (3.0 mmoles) of 7-[4-(4-fluorophenyl)-6-isopropyl-2-(methanesulphonyl-methyl-amino)-pyrimidin-5-yl]-(3R,5S)-dihydroxy-hept-6-enoic acid tert.-butylammonium salt are added under vigorous stirring at 0° C. After the complete dissolution of the starting compound, 5×1.5 ml (5×7.5 mmoles) of a saturated calcium chloride solution is added dropwise at 15-minute intervals. After the dosage, the mixture is stirred for a further hour at 0° C., then the upper layer containing ethyl acetate is separated and washed with 5 ml of 2.0 M calcium chloride solution, then 2×5 ml of water. The dehydration of the organic layer is carried out by azeotropic distillation in such a way that the phase containing ethylacetate is evaporated to dryness and the obtained white residue is dissolved in 5 ml of anhydrous ethyl acetate. The solution is stirred for 5 minutes, then evaporated to dryness at 42-45° C. under 50 mbar pressure. To the residue 6 ml of cyclohexane is added and the suspension is stirred for 30 minutes. The solid product is filtered off, washed with 5 ml of anhydrous cyclohexane and dried at 50° C. for 7 hours under vacuum, thus 1.13 g (75%) product is obtained.

HPLC purity: 99.87%.
Diastereomer contaminant: 0.02%.
Rosuvastatin lactone contaminant: 0.02%.
Tert.-butylamin content: 68 ppm.
Humidity: 1.05%.

Example 3

7-[4-(4-Fluorophenyl)-6-isopropyl-2-(methane-sulphonyl-methyl-amino)-pyrimidin-5-yl]-(3R,5S)-dihydroxy-hept-6-enoic acid Calcium Salt (2:1)

Into a two-layer mixture of 10 ml of water and 15 ml of ethyl acetate 1.67 g (3.0 mmoles) of 7-[4-(4-fluorophenyl)-6-isopropyl-2-(methanesulphonyl-methyl-amino)-pyrimidin-5-yl]-(3R,5S)-dihydroxy-hept-6-enoic acid tert-butylammonium salt are added under vigorous stirring at 40° C. After the complete dissolution of the starting compound, 5×1.5 ml (5×7.5 mmoles) of a saturated calcium chloride solution are added dropwise at 15-minute intervals.

After the dosage, the mixture is stirred for a further hour at 40° C., then the upper layer containing ethyl acetate is separated and washed with 5 ml of 2.0 M calcium chloride solution, then 2×5 ml of water. The dehydration of the organic layer is carried out by azeotropic distillation in such a way that the phase containing ethylacetate is evaporated to dryness and the obtained white residue is dissolved in 5 ml of anhydrous ethyl acetate. The solution is stirred for 5 minutes, then evaporated to dryness at 42-45° C. under 50 mbar pressure. To the residue, 6 ml of cyclohexane are added and the suspension is stirred for 30 minutes. The solid product is filtered off, washed with 5 ml of anhydrous cyclohexane and dried at 50° C. for 7 hours under reduced pressure, thus 1.25 g (83%) product is obtained.

HPLC purity: 99.85%.
Diastereomer contaminant: 0.03%.
Rosuvastatin lactone contaminant: 0.05%.
Tert-butylamin content: 127 ppm.
Humidity: 1.40%.

Example 4

7-[4-(4-Fluorophenyl)-6-isopropyl-2-(methane-sulphonyl-methyl-amino)-pyrimidin-5-yl]-(3R,5S)-dihydroxy-hept-6-enoic acid Calcium Salt (2:1)

Into a two-layer mixture of 10 ml of water and 15 ml of ethyl acetate 1.67 g (3.0 mmoles) of 7-[4-(4-fluorophenyl)-6-isopropyl-2-(methanesulphonyl-methyl-amino)-pyrimidin-5-yl]-(3R,5S)-dihydroxy-hept-6-enoic acid tert-butylammonium salt is added under vigorous stirring at room temperature. After the complete dissolution of the starting compound, 3×0.4 g (3×2.5 mmoles) of solid calcium acetate are added to the solution at 15-minute intervals. After the dosage, the mixture is stirred for a further hour at room temperature, then the upper layer containing ethyl acetate is separated and washed with 3×5 ml of water. The dehydration of the organic layer is carried out by azeotropic distillation in such a way that the phase containing ethyl acetate is evaporated to dryness and the obtained white residue is dissolved in 5 ml of anhydrous ethyl acetate. The solution is stirred for 5 minutes, then evaporated to dryness at 42-45° C. under 50 mbar pressure. To the residue, 6 ml of cyclohexane are added and the suspension is stirred for 30 minutes. The solid product is filtered off, washed with 5 ml of anhydrous cyclohexane and dried at 50° C. for 7 hours under reduced pressure, thus 1.36 g (91%) product is obtained.

HPLC purity: 99.27%.
Diastereomer contaminant: 0.05%.
Rosuvastatin lactone contaminant: 0.08%.
Tert-butylamin content: 566 ppm.
Humidity: 2.21%.

Example 5

7-[4-(4-Fluorophenyl)-6-isopropyl-2-(methane-sulphonyl-methyl-amino)-pyrimidin-5-yl]-(3R,5S)-dihydroxy-hept-6-enoic acid Calcium Salt (2:1)

Into a two-layer mixture of 10 ml of water and 15 ml of ethyl acetate, 1.67 g (3.0 mmoles) of 7-[4-(4-fluorophenyl)-6-isopropyl-2-(methanesulphonyl-methyl-amino)-pyrimidin-5-yl]-(3R,5S)-dihydroxy-hept-6-enoic acid tert-butylammonium salt is added under vigorous stirring at room temperature. After the complete dissolution of the starting compound, 1.1 g (15 mmoles) of calcium hydroxide is added to the biphase solution. After the dosage, the mixture is stirred for a further hour at room temperature, then the upper layer containing ethyl acetate is separated and washed with 3×5 ml of water. The dehydration of the organic layer is carried out by azeotropic distillation in such a way that the phase containing ethyl acetate is evaporated to dryness and the obtained white residue is dissolved in 5 ml of anhydrous ethyl acetate. The solution is stirred for 5 minutes, then evaporated to dryness at 42-45° C. under 50 mbar pressure. To the residue, 6 ml of cyclohexane is added and the suspension is stirred for 30 minutes. The solid product is filtered off, washed with 5 ml of anhydrous cyclohexane and dried at 50° C. for 7 hours under reduced pressure, thus 0.65 g (43%) product is obtained.

HPLC purity: 99.69%.
Diastereomer content: 0.10%.
Rosuvastatin lactone contaminant: 0.11%.
Tert.-butylamin content: 4922 ppm.

Example 6

7-[4-(4-Fluorophenyl)-6-isopropyl-2-(methane-sulphonyl-methyl-amino)-pyrimidin-5-yl]-(3R,5S)-dihydroxy-hept-6-enoic acid Calcium Salt (2:1)

Into a two layer mixture of 10 ml of water and 15 ml of ethyl acetate 1.67 g (3.0 mmoles) of 7-[4-(4-fluorophenyl)-6-isopropyl-2-(methanesulphonyl-methyl-amino)-pyrimidin-5-yl]-(3R,5S)-dihydroxy-hept-6-enoic acid tert-butylammonium salt is added under vigorous stirring at room temperature. After the complete dissolution of the starting compound 2×1.5 ml (2×7.5 mmoles) of saturated calcium chloride solution are added dropwise at 15-minute intervals. After the dosage, the mixture is stirred for a further hour at room temperature, then the upper layer containing ethyl acetate is separated and washed with 5 ml of 2.0 M calcium chloride solution, and 2×5 ml of water. The dehydration of the organic layer is carried out by azeotropic distillation in such a way that the layer containing ethylacetate is evaporated to dryness and the obtained white residue is dissolved in 5 ml of anhydrous ethyl acetate. The solution is stirred for 5 minutes, then evaporated to dryness at 42-45° C. under 50 mbar pressure. To the residue, 6 ml of methyl-tert.-butyl ether are added and the suspension is stirred for 30 minutes. The solid product is filtered off, washed with 5 ml of anhydrous methyl-tert.-butyl ether and dried at 50° C. for 7 hours under reduced pressure, thus 1.05 g (70%) product is obtained.

HPLC purity: 99.88%.
Diastereomer contaminant: 0.02%.
Rosuvastatin lactone contaminant: 0.04%.
Tert.-butylamin content: 648 ppm.
Humidity: 1.50%.

Example 7

7-[4-(4-Fluorophenyl)-6-isopropyl-2-(methane-sulphonyl-methyl-amino)-pyrimidin-5-yl]-(3R,5S)-dihydroxy-hept-6-enoic acid Calcium Salt (2:1)

Into a two layer mixture of 30 ml of water and 45 ml of ethyl acetate 5 g (9.0 mmoles) of 7-[4-(4-fluorophenyl)-6-isopropyl-2-(methanesulphonyl-methyl-amino)-pyrimidin-5-yl]-(3R,5S)-dihydroxy-hept-6-enoic acid tert-butylammonium salt is added under vigorous stirring at room temperature. After the complete dissolution of the starting compound, 5×4.5 ml (5×7.5 mmoles) of saturated calcium chloride solution is added dropwise at 15-minute intervals. After the dosage, the mixture is stirred for a further hour at room temperature, then the upper layer containing ethyl acetate is separated and 15 ml of 2.0 M calcium chloride solution is added and stirred for a further hour. The phases are separated and the organic phase is washed with 2×15 ml of water. The dehydration of the organic layer is carried out by azeotropic distillation in such a way that the phase containing ethylacetate is evaporated to dryness and the obtained white residue is dissolved in 15 ml of anhydrous ethyl acetate. The solution is stirred for 5 minutes, then evaporated to dryness at 42-45° C. under 50 mbar pressure. To the residue 18 ml of cyclohexane is added and the suspension is stirred for 30 minutes. The solid product is filtered off, washed with 5 ml of anhydrous cyclohexane and dried at 50° C. for 7 hours under reduced pressure, thus 4.37 g (97%) product is obtained.

HPLC purity: 99.83%.
Diastereomer contaminant: 0.03%.
Rosuvastatin lactone contaminant: 0.04%.
Tert.-butylamine content: 204 ppm.
Humidity: 1.90%.

Example 8

7-[4-(4-Fluorophenyl)-6-isopropyl-2-(methane-sulphonyl-methyl-amino)-pyrimidin-5-yl]-(3R,5S)-dihydroxy-hept-6-enoic acid Calcium Salt (2:1)

Into a two layer mixture of 90 ml of water and 150 ml of ethyl acetate 15 g (27 mmoles) of 7-[4-(4-fluorophenyl)-6-isopropyl-2-(methanesulphonyl-methyl-amino)-pyrimidin-5-yl]-(3R,5S)-dihydroxy-hept-6-enoic acid tert-butylammonium salt is added under vigorous stirring at room temperature and protected from light. After the complete dissolution of the starting compound, 2×13.5 ml (2×27 mmoles) of 2.0M calcium chloride solution are added dropwise at 15-minute intervals. After the dosage, the mixture is stirred for a further hour at room temperature, then the upper layer containing ethyl acetate is separated and washed with 45 ml of 2 M calcium chloride solution and 2×45 ml of water. The dehydration of the organic layer is carried out by azeotropic distillation in such a way that the phase containing ethyl acetate is evaporated to dryness and the obtained white solid residue is dissolved in 45 ml of anhydrous ethyl acetate. The solution is stirred for 5 minutes, then evaporated to dryness at 42-45° C. under 50 mbar pressure and protected from light. To the residue 54 ml of anhydrous cyclohexane is added and the suspension is stirred for 30 minutes. The solid product is filtered off, washed with 45 ml of anhydrous cyclohexane and dried at 50° C. for 7 hours under reduced pressure. After drying 13.1 g (97%) product are obtained.

HPLC purity: 99.88%.
Diastereomer contaminant: 0.02%.
Rosuvastatin lactone contaminant: 0.04%.
Tert.-butylamine content: 115 ppm.
Humidity: 0.91%.

Example 9

7-[4-(4-Fluorophenyl)-6-isopropyl-2-(methane-sulphonyl-methyl-amino)-pyrimidin-5-yl]-(3R,5S)-dihydroxy-hept-6-enoic acid Calcium Salt (2:1)

Into a two layer mixture of 10 ml of water and 15 ml of ethyl acetate 1.67 g (3.0 mmoles) of rosuvastatin tert-butylammonium salt are added under vigorous stirring at room temperature and protected from light.

Into the mixture, 4.45 ml (157 equiv.) of saturated calcium chloride solution are added dropwise. After the dosage, the mixture is stirred for further two hours at room temperature, then the upper layer containing ethyl acetate is separated and washed with 5 ml of 2 M calcium chloride solution and 2×5 ml of water. The organic phase is evaporated until the residue becomes a thick suspension, 3.3 ml of ethyl acetate are added and the mixture stirred for 5 minutes then evaporated to a thick suspension at 42-45° C. under 50 mbar pressure and protected from light. To the residue, 5.5 ml of cyclohexane is added to and evaporated to a thick suspension. Into the slurry, 6.6 ml of cyclohexane is added and stirred for 20 minutes, then 6 ml of cyclohexane is distilled off at 42-45° C. under 50 mbar pressure and protected from light. To this slurry, 6.6 ml of cyclohexane are added and stirred for 20 minutes, then the cyclohexane is distilled off. To the solid residue, 10 ml of water are added and the mixture is stirred for 30 minutes, then filtered. The product is dried for 7 hours at 50° C., under $10^{-2}$ mbar pressure. After drying 1.45 g (97%) product are obtained.

HPLC purity: 99.86%.
Diastereomer contaminant: 0.02%.
Rosuvastatin lactone contaminant: 0.03%.
Tert.-butylamine content: 115 ppm.
Humidity: 1.59%.

Example 10

7-[4-(4-Fluorophenyl)-6-isopropyl-2-(methane-sulphonyl-methyl-amino)-pyrimidin-5-yl]-(3R,5S)-dihydroxy-hept-6-enoic acid Zinc Salt (2:1)

Under stirring, 50 ml of ethyl acetate is added to 5.0 g (9.0 mmoles) of 7-[4-(4-Fluorophenyl)-6-isopropyl-2-(methane-sulphonyl-methyl-amino)-pyrimidin-5-yl]-(3R,5S)-dihydroxy-hept-6-enoic acid ter t-butylammonium salt at 25° C. Then 15.3 ml water are added to the suspension. A clear two-layer mixture is formed, into which 5.5 ml (12.24 mmoles) of 2.23 M aqueous $ZnSO_4$ solution are added dropwise in ten minutes. The reaction mixture is stirred for an hour vigorously, then the layers are separated and the organic phase is washed with 2×10 ml of 2.23 M aqueous $ZnSO_4$ solution, then 10 ml of water. The dehydration of the organic layer is carried out by azeotropic distillation in such a manner that the half of the solvent is evaporated, then 150 ml of ethyl acetate are being added and evaporated continuously as an azeotropic distillate in vacuum at 50° C. under 50-70 mbar to a thick suspension. To the residue, 10 ml of ethylacetate are added and stirred for 5 minutes, evaporated, then washed with 2×10 ml of cyclohexane. The product is dried at 50° C. for 7 hours under vacuum. Thus 3.5 g (77%) product are obtained.

IR (KBr): 3423, 1546, 1381, 1156 $cm^{-1}$.

$^1$H-NMR (DMSO-$d_6$, 500 MHz): δ 7.72 (dd, J=7.7; 5.9 Hz, 4H), 7.27 (t, J=8.5 Hz, 4H), 6.52 (d, J=15.9 Hz, 2H), 5.54 (dd, J=15.9; 5.1 Hz, 2H), 4.94 (br s, 4H), 4.21 (m, 2H), 3.84 (m, 2H), 3.55 (s, 6H), 3.46 (s, 6H), 3.40 (m, 2H), 2.26 (d, J=13.7 Hz, 2H), 2.16 (dd, J=14.5; 7.7 Hz, 2H), 1.52 (m, 2H), 1.38 (m, 2H), 1.22 (d, J=6.4 Hz, 12H) ppm.

HPLC purity: 99.83%.
Diastereomer contaminant: 0%.
Rosuvastatin lactone contaminant: 0.12%.
Tert-butylamine content: 52 ppm.
Humidity: 1.13%.

Example 11

7-[4-(4-Fluorophenyl)-6-isopropyl-2-(methane-sulphonyl-methyl-amino)-pyrimidin-5-yl]-(3R,5S)-dihydroxy-hept-6-enoic acid Zinc Salt (2:1)

Under stirring, 50 ml of ethyl acetate aer added to 5.0 g (9.0 mmoles) of 7-[4-(4-Fluorophenyl)-6-isopropyl-2-(methane-sulphonyl-methyl-amino)-pyrimidin-5-yl]-(3R,5S)-dihydroxy-hept-6-enoic acid tert-butylammonium salt at 25° C. Then 15.3 ml water are added to the suspension. A clear two layer mixture is formed into which 5.5 ml (12.24 mmoles) of 2.23 M aqueous $ZnSO_4$ solution are added dropwise during ten minutes. The reaction mixture is stirred for an hour under vigorous stirring, then the phases are separated and the organic phase is washed with 2×10 ml of 2.23 M aqueous ZnSO$_4$ solution, then 10 ml of water. The dehydration of the organic layer is carried out by azeotropic distillation in vacuum at 50° C. under 50-70 mbar using a discontinuous process as follows. First the organic phase is evaporated to dryness, then the residue is dissolved in 50 ml of ethyl acetate and then evaporated to a gelled suspension state, then 30 ml of ethyl acetate is added and stirred for 5 minutes, then evaporated again until becoming a thick suspension, then further 20 ml of ethyl acetate is added and stirred for 5 minutes, then filtered. The product is washed with 5 ml and 2×10 ml of cyclohexane. The product is dried at 50° C. for 7 hours under reduced pressure, 3.95 g (86%) product are obtained.

HPLC purity: 99.81%.
Diastereomer contaminant: 0%.
Rosuvastatin lactone contaminant: 0.13%.
Tert.-butylamine content: 66 ppm.
Humidity: 0.87%.

Example 12

7-[4-(4-Fluorophenyl)-6-isopropyl-2-(methane-sulphonyl-methyl-amino)-pyrimidin-5-yl]-(3R,5S)-dihydroxy-hept-6-enoic acid Zinc Salt (2:1)

Under stirring, 50 ml of ethyl acetate is added to 5.0 g (9.0 mmoles) of 7-[4-(4-Fluorophenyl)-6-isopropyl-2-(methane-sulphonyl-methyl-amino)-pyrimidin-5-yl]-(3R,5S)-dihydroxy-hept-6-enoic acid tert-butylammonium salt at 25° C. Then 15.3 ml water are added to the suspension. A clear two layer mixture is formed, into which 9.2 ml (20.34 mmoles) of 2.23 M aqueous ZnSO$_4$ solution are added dropwise during ten minutes. The reaction mixture is stirred for an hour under vigorous stirring, then the layers are separated and the organic layer is washed with 2×10 ml of 2.23 M aqueous ZnSO$_4$ solution, then 10 ml of water. The dehydration of the organic layer is carried out by azeotropic distillation in such a way that the half of the solvent is evaporated, then 150 ml of ethyl acetate is being added and evaporated continuously as azeotropic distillate at 50° C. under 50-70 mbar vacuum to a thick suspension. Then 10 ml of ethyl acetate is added to the residue, stirred for 5 minutes and filtered. The product is washed with 2×10 ml of cyclohexane. The product is dried at 50° C. for 7 hours under reduced pressure, and 3.37 g (73%) is obtained.

HPLC purity: 99.80%.
Diastereomer contaminant: 0.06%.
Rosuvastatin lactone contaminant: 0.14%.
Tert.-butylamine content: 54 ppm.
Humidity: 1.30%.

Example 13

7-[4-(4-Fluorophenyl)-6-isopropyl-2-(methane-sulphonyl-methyl-amino)-pyrimidin-5-yl]-(3R,5S)-dihydroxy-hept-6-enoic acid Zinc Salt (2:1)

Under stirring, 50 ml of ethyl acetate are added to 5.0 g (9.0 mmoles) of 7-[4-(4-Fluorophenyl)-6-isopropyl-2-(methane-sulphonyl-methyl-amino)-pyrimidin-5-yl]-(3R,5S)-dihydroxy-hept-6-enoic acid tert-butylammonium salt at 25° C. Then 15.3 ml water is added to the suspension. A clear two layer mixture is formed, to which 9.2 ml (20.34 mmoles) of 2.23 M aqueous ZnSO$_4$ solution are added dropwise during ten minutes. The reaction mixture is stirred for an hour vigorously, then the phases are separated and the organic phase is washed with 2×10 ml of 2.23 M aqueous ZnSO$_4$ solution, then 10 ml of water. The dehydration of the organic layer is carried out by azeotropic distillation in vacuum at 50° C. under 50-70 mbar using a discontinuous process as follows. First the organic phase is evaporated to dryness, then the residue is dissolved in 50 ml of ethyl acetate and then evaporated to a gelled suspension state, then 30 ml of ethyl acetate is added and stirred for 5 minutes, then evaporated again until becoming a thick suspension then further 20 ml of ethyl acetate is added and stirred for 5 minutes and filtered. The product is washed with 5 ml and 2×10 ml of cyclohexane. The product is dried at 50° C. for 7 hours under reduced pressure, and 3.31 g (72%) is obtained.

(HPLC: 99.74%).
HPLC purity: 99.74%.
Diastereomer contaminant: 0.07%.
Rosuvastatin lactone contaminant: 0.40%.
Tert.-butylamine content: 53 ppm.
Humidity: 1.10%.

Example 14

7-[4-(4-Fluorophenyl)-6-isopropyl-2-(methane-sulphonyl-methyl-amino)-pyrimidin-5-yl]-(3R,5S)-dihydroxy-hept-6-enoic acid Zinc Salt (2:1)

Under stirring, 50 ml of ethyl acetate is added to 5.0 g (9.0 mmoles) of 7-[4-(4-Fluorophenyl)-6-isopropyl-2-(methane-sulphonyl-methyl-amino)-pyrimidin-5-yl]-(3R,5S)-dihydroxy-hept-6-enoic acid tert-butylammonium salt at 25° C. Then 15.3 ml water are added to the suspension. A clear two layer mixture is formed, to which 5.5 ml (12.24 mmoles) of 2.23 M aqueous ZnSO$_4$ solution are added dropwise during ten minutes. The reaction mixture is stirred for an hour vigorously, then the phases are separated and the organic phase is washed with 2×10 ml of 2.23 M aqueous ZnSO$_4$ solution, then 10 ml of water. The drying of the organic phase is carried out using heated ZnSO$_4$ in such a manner that 2.0 g of heated ZnSO$_4$ is added first to the organic phase and stirred for 30 minutes, then filtered, then 1.0 g of heated ZnSO$_4$ is added and stirred again for 30 minutes and filtered. The solution containing ethyl acetate is evaporated in vacuum to give a crystalline suspension, wherein 30 ml of ethyl acetate is added, stirred for 5 minutes and filtered. The product is washed with 5 ml and 2×10 ml of cyclohexane. The product is dried at 50° C. for 7 hours under reduced pressure, and 3.64 g (79%) is obtained.

HPLC purity: 99.58%.
Diastereomer contaminant: 0.04%.
Rosuvastatin lactone contaminant: 0.37%.
Tert.-butylamine content: 415 ppm.
Humidity: 1.24%.

Reference Example 1

7-[4-(4-Fluorophenyl)-6-isopropyl-2-(methane-sulphonyl-methyl-amino)-pyrimidin-5-yl]-(3R,5S)-dihydroxy-hept-6-enoic acid Calcium Salt (2:1)

Under stirring, 1.67 g (3.0 mmoles) of 7-[4-(4-Fluorophenyl)-6-isopropyl-2-(methanesulphonyl-methyl-amino)-pyrimidin-5-yl]-(3R,5S)-dihydroxy-hept-6-enoic acid tert-butylammonium salt are added to 25 ml of ethanol at room temperature. After ten minutes stirring, 3.0 ml (3.0 mmoles) of 1.0 M calcium chloride solution are added dropwise. The reaction mixture is stirred for a further hour. The separated white precipitate is filtered off and dried at 50° C. for 7 hours. After drying 0.60 g (40%) product is obtained.
HPLC purity: 99.78%.
Diastereomer contaminant: 0.05%.
Rosuvastatin lactone contaminant: 0.05%.
Tert.-butylamine content: 648 ppm.

Reference Example 2

7-[4-(4-Fluorophenyl)-6-isopropyl-2-(methane-sulphonyl-methyl-amino)-pyrimidin-5-yl]-(3R,5S)-dihydroxy-hept-6-enoic acid Calcium Salt (2:1)

Under stirring, 1.67 g (3.0 mmoles) of 7-[4-(4-Fluorophenyl)-6-isopropyl-2-(methanesulphonyl-methyl-amino)-pyrimidin-5-yl]-(3R,5S)-dihydroxy-hept-6-enoic acid tert-butylammonium salt are added to 25 ml of ethanol at room temperature. After ten minutes stirring, a solution of 1.0 g (6.3 mmoles) of calcium chloride in 10 ml of water is added dropwise. The reaction mixture is stirred for an hour, then 20 ml of the organic solvent are evaporated. The separated white precipitate is filtered and dried under vacuum at 50° C. for 7 hours. After drying 0.36 g (24%) product is obtained.
HPLC purity: 99.42%.
Diastereomer contaminant: 0.05%.
Rosuvastatin lactone contaminant: 0.15%.
Tert.-butylamine content: 587 ppm.

Reference Example 3

7-[4-(4-Fluorophenyl)-6-isopropyl-2-(methane-sulphonyl-methyl-amino)-pyrimidin-5-yl]-(3R,5S)-dihydroxy-hept-6-enoic acid Calcium Salt (2:1)

Under stirring, 1.67 g (3.0 mmoles) of 7-[4-(4-Fluorophenyl)-6-isopropyl-2-(methanesulphonyl-methyl-amino)-pyrimidin-5-yl]-(3R,5S)-dihydroxy-hept-6-enoic acid tert-butylammonium salt are added to 60 ml of water at room temperature. After ten minutes stirring, a solution of 3.0 g (3.0 mmoles) of 1.0 M calcium chloride solution are added dropwise. The reaction mixture is stirred for a further hour. The separated white precipitate is filtered and dried under vacuum at 50° C. for 7 hours. After drying 0.95 g (63%) product is obtained.
HPLC purity: 98.99%.
Diastereomer contaminant: 0.05%.
Rosuvastatin lactone contaminant (before drying): 0.05%.
Tert.-butylamine content: 1937 ppm.
Humidity: 3.09%.

Reference Example 4

7-[4-(4-Fluorophenyl)-6-isopropyl-2-(methane-sulphonyl-methyl-amino)-pyrimidin-5-yl]-(3R,5S)-dihydroxy-hept-6-enoic acid Calcium Salt (2:1)

Under stirring, 5.0 g (9.0 mmoles) of 7-[4-(4-Fluorophenyl)-6-isopropyl-2-(methanesulphonyl-methyl-amino)-pyrimidin-5-yl]-(3R,5S)-dihydroxy-hept-6-enoic acid tert-butylammonium salt is added to 200 ml of water at room temperature. After ten minutes stirring, a solution of 9.0 g (9.0 mmoles) of 1.0 M calcium chloride solution are added dropwise. The reaction mixture is stirred for a further hour. The separated white precipitate is filtered and dried under vacuum at 50° C. for 7 hours. After drying, 3.0 g (68%) product is obtained.
HPLC purity: 99.23%.
Diastereomer contaminant: 0.05%.
Rosuvastatin lactone contaminant (before drying): 0.24%.
Tert.-butylamine content: 3018 ppm.
Humidity: 4.05%.

Reference Example 5

7-[4-(4-Fluorophenyl)-6-isopropyl-2-(methane-sulphonyl-methyl-amino)-pyrimidin-5-yl]-(3R,5S)-dihydroxy-hept-6-enoic acid Zinc Salt (2:1)

Under stirring, 250 ml of water are added to 2.5 g (4.5 mmoles) of 7-[4-(4-Fluorophenyl)-6-isopropyl-2-(methanesulphonyl-methyl-amino)-pyrimidin-5-yl]-(3R,5S)-dihydroxy-hept-6-enoic acid tert-butylammonium salt at 25° C. A thin suspension is obtained in 15 minutes, then 2.75 ml (6.12 mmoles) of 2.23 M aqueous $ZnSO_4$ solution are added dropwise during ten minutes. The product is precipitating continuously during the addition. After one hour stirring, the precipitate is filtered off and washed with 3×10 ml of water, then dried under vacuum at 50° C. for 7 hours, thus 2.30 g (86%) product is obtained.
HPLC purity: 99.30%.
Diastereomer contaminant: 0.12%.
Rosuvastatin lactone contaminant: 0.51%.
Humidity: 2.20%.

Reference Example 6

Reproduction of Example 4 of the International patent application No. WO 2004/014872 Using Rosuvastatin Tert.Butyl Ammonium Salt as Starting Material 7-[4-(4-Fluorophenyl)-6-isopropyl-2-(methane-sulphonyl-methyl-amino)-pyrimidin-5-yl]-(3R,5S)-dihydroxy-hept-6-enoic acid Calcium Salt (2:1)

1.67 g (3 mmoles) of 7-[4-(4-Fluorophenyl)-6-isopropyl-2-(methanesulphonyl-methyl-amino)-pyrimidin-5-yl]-(3R,5S)-dihydroxy-hept-6-enoic acid tert-butylammonium salt are dissolved in 12 ml of distilled water at room temperature, then the solution is heated to 40° C. A solution of 0.26 g (1.7 mmole) of calcium chloride dehydrate in 2.5 ml of water is added dropwise at 40° C. during 5 minutes. The mixture is stirred for 15 minutes, allowed to cool to room temperature during an hour, then stirred for a further hour at room temperature. The formed solid compound is filtered, washed with 14 ml of water under nitrogen gas, thus 1.05 g (70%) product are obtained.
Tert.-butylamine content: 40000 ppm.
Humidity: 3.30%.

Reference Example 7

Reproduction of Example 14 of the International patent application No. WO 2006/136407 Using Rosuvastatin Tert.Butyl Ammonium Salt as Starting Material 7-[4-(4-Fluorophenyl)-6-isopropyl-2-(methane-sulphonyl-methyl-amino)-pyrimidin-5-yl]-(3R,5S)-dihydroxy-hept-6-enoic acid Calcium Salt (2:1)

2.0 g (3.7 mmoles) of 7-[4-(4-Fluorophenyl)-6-isopropyl-2-(methanesulphonyl-methyl-amino)-pyrimidin-5-yl]-(3R,5S)-dihydroxy-hept-6-enoic acid tert.-butylammonium salt is added to 13 ml of distilled water and 2 ml of 1.0 M calcium acetate solution.
The reactants are dissolved under vigorous stirring and nitrogen atmosphere at room temperature, then stirred for ten minutes at 10° C. The formed white precipitate is filtered and washed with 2 ml of water. It is dried on the sieve for an hour and then between 50-60° C. under 10 mbar pressure for 2 hours. The product: 1.48 g (82%) amorphous rosuvastatin calcium salt.

Tert.-butylamine content: 62000 ppm.
Humidity: 0.40%.

Reference Example 8

7-[4-(4-Fluorophenyl)-6-isopropyl-2-(methane-sulphonyl-methyl-amino)-pyrimidin-5-yl]-(3R,5S)-dihydroxy-hept-6-enoic acid Zinc Salt (2:1)

To 31.06 g (56.7 mmoles) of 7-[4-(4-Fluorophenyl)-6-isopropyl-2-(methanesulphonyl-methyl-amino)-pyrimidin-5-yl]-(3R,5S)-dihydroxy-hept-6-enoic acid sodium salt are added to 400 ml water under stirring at 25° C. To the colourless solution, 26.0 ml (26 mmole) of 1.0 M $ZnSO_4$ solution are added dropwise during 15 minutes. The precipitated white crystals are filtered, washed twice, then dried under vacuum at room temperature for 16 hours, thus 25.82 g product is obtained.

The invention claimed is:

1. A process for the preparation of rosuvastatin salts of the Formula (I)

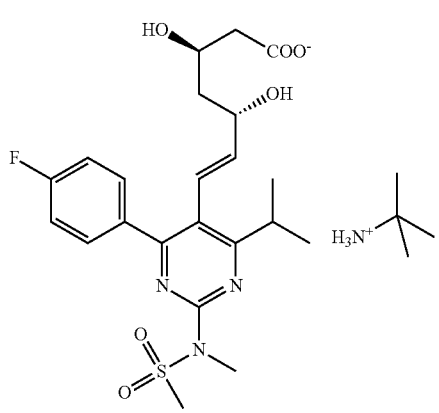

with bivalent cations which comprises the steps of:
(a) reacting the rosuvastatin tert-butyl-ammonium salt of the formula (IV)

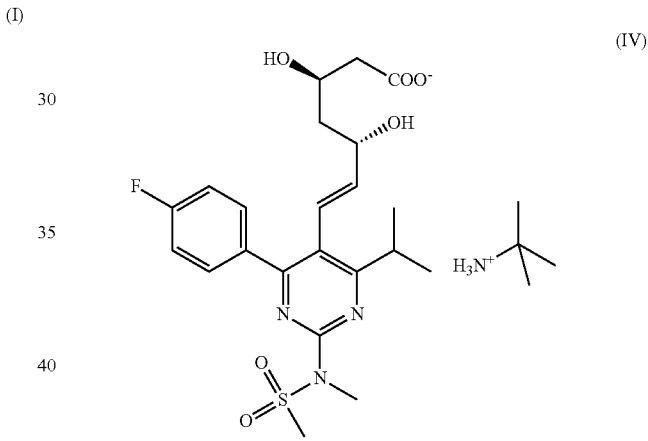

with a bivalent cation, in a two-phase mixture of a water immiscible or slightly miscible solvent and water, and
(b) isolating the obtained salt.

2. A process for the preparation of rosuvastatin calcium salt of the formula (II)

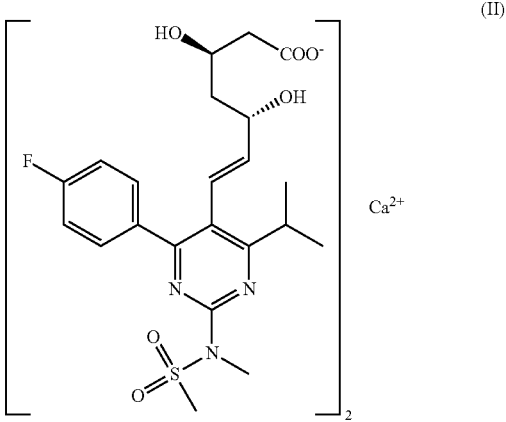

which comprises the steps of;
(a) reacting the rosuvastatin tert.-butyl ammonium salt of the formula (IV)

with a calcium ion source in a two phase mixture of a water immiscible or slightly miscible organic solvent and water, to obtain the rosuvastatin calcium salt of the Formula (II), and
(b) separating the obtained salt.

3. The process according to claim 2, wherein calcium hydroxide, or calcium salts of organic or inorganic acids, are used as the calcium ion source.

4. The process according to claim 2 wherein the amount of the calcium ion source used is 0.45-50 molar equivalents of the molar amount of the used compound of the formula (IV).

5. The process according to claim 2 wherein the process is carried out at a temperature between 0° C. and 50° C.

6. The process according to claim 2 wherein the process is carried out in a two phase mixture of water and ethyl acetate.

7. The process according to claim 2 wherein the rosuvastatin calcium salt according to the formula (II) obtained from an organic solvent is dried with azeotropic distillation.

8. The process according to claim 2 wherein the organic phase containing rosuvastatin calcium salt and ethyl acetate as the organic solvent according to the formula (II) is dried with a desiccant.

9. A process for the preparation of rosuvastatin calcium salt of the Formula (II)

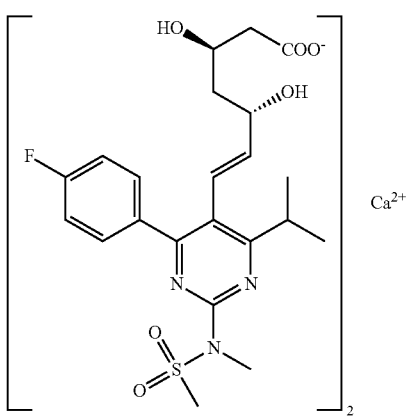

(II)

wherein a two phase mixture of a water immiscible organic solvent and water, in a ratio of 5:1-5:4 (v/v), is added to the rosuvastatin tert-butyl ammonium salt of the formula (IV)

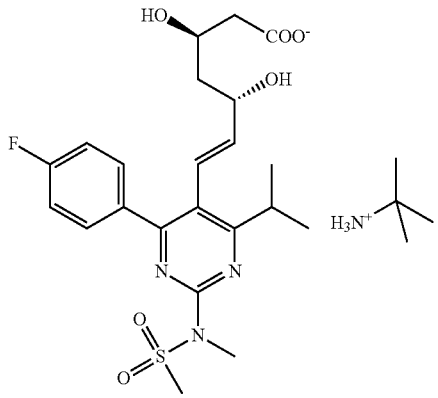

(IV)

at a temperature between 0° C. and 50° C., then 0.45-0.50 molar equivalents of a calcium ion source is added, based on the amount of the used starting compound, the mixture is stirred for 0.01-10 hours at a temperature between 0° C. and 50° C., then the organic and aqueous phases are separated, optionally the organic phase is washed once or several times with a solution of calcium salt and/or water or optionally the organic phase is dried with a desiccant, the organic phase is evaporated, and if desired, the water content of the obtained rosuvastatin calcium salt is reduced by a single or repeated addition and total or partial evaporation of an organic solvent, and optionally stirring the product with an apolar solvent, filtering the product, and optionally washing and drying the product.

10. A process for the preparation of a rosuvastatin zinc salt of the formula (III)

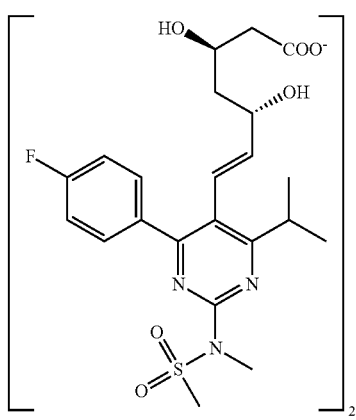

(III)

which comprises the steps of: (a) reacting the rosuvastatin tert-butyl ammonium salt of the formula (IV)

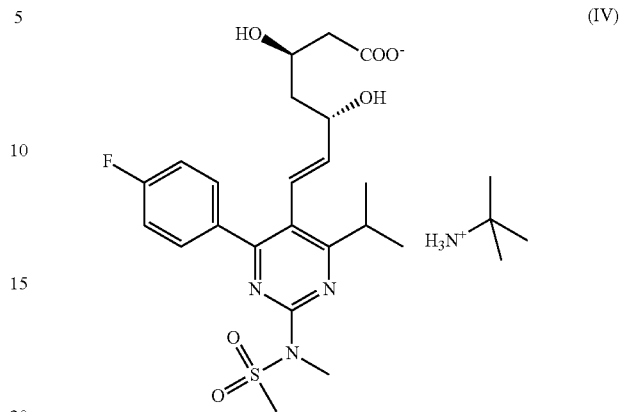

(IV)

with a zinc ion source in a two-phase mixture of a water immiscible or slightly miscible solvent and water to obtain the rosuvastatin zinc salt of the Formula (III), and (b) separating the obtained salt.

11. The process according to claim 10 wherein zinc salts of organic or inorganic acids are used as the zinc ion source.

12. The process according to claim 10 wherein the amount of the zinc ion source used is 0.45-50 molar equivalents of the molar amount of the used compound of the formula (IV).

13. The process according to claim 10 wherein the process is carried out at a temperature between 0° C. and 50° C.

14. The process according to claim 10 wherein the rosuvastatin zinc salt according to the formula (III) obtained from an organic solvent is dried by azeotropic distillation.

15. The process according to claim 10 wherein the organic phase containing rosuvastatin zinc salt of the formula (III) and ethyl acetate is dried with a desiccant.

16. A process for the preparation of rosuvastatin zinc salt of the formula (III)

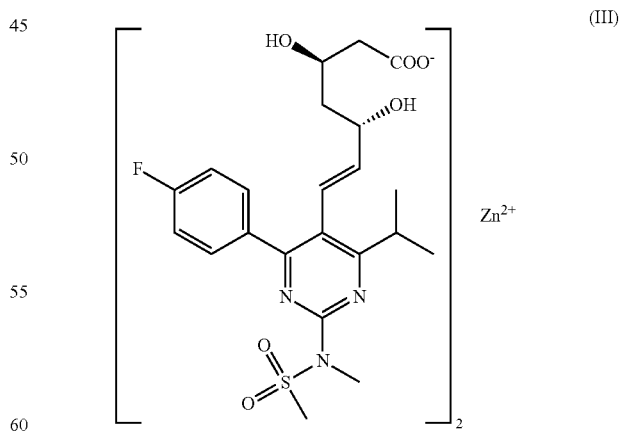

(III)

wherein a two phase mixture of a water immiscible organic solvent and water, in a ratio of 5:1-5:4 (v/v), is added to the rosuvastatin tert-butyl ammonium salt of the Formula (IV)

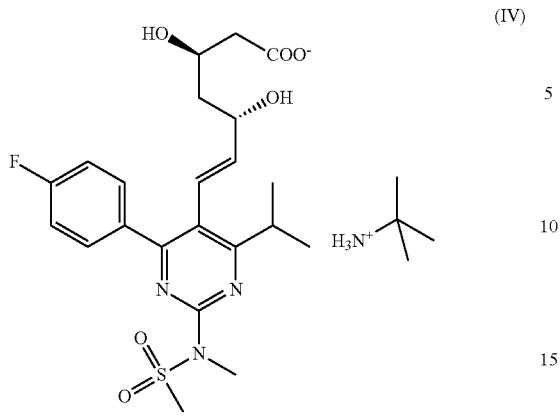

(IV)

at a temperature between 0° C. and 5° C., then 0.45-0.50 molar equivalents of zinc ion source are added for each mole of the starting compound, the mixture is stirred for 0.1-2 hours at a temperature between 0° C. and 50° C. the organic phase is separated, washed once or several times with a solution of a zinc salt and/or optionally with water or the organic layer is dried with a desiccant, evaporated, and if desired, the water content of the obtained rosuvastatin zinc salt is reduced by single or repeated addition and total or partial evaporation of an organic solvent optionally the thus obtained rosuvastatin zinc salt is stirred with an apolar organic solvent, filtering the product and optionally washing and drying the product.

* * * * *

UNITED STATES PATENT AND TRADEMARK OFFICE
CERTIFICATE OF CORRECTION

PATENT NO. : 8,507,513 B2
APPLICATION NO. : 13/143943
DATED : August 13, 2013
INVENTOR(S) : Kovanyine Lax et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 75 days.

Signed and Sealed this

Fifteenth Day of September, 2015

Michelle K. Lee
*Director of the United States Patent and Trademark Office*